United States Patent [19]
Woodward

[11] Patent Number: 6,124,353
[45] Date of Patent: Sep. 26, 2000

[54] METHOD OF TREATING OCULAR HYPERTENSION WITH 8-EPI PROSTAGLANDINS

[75] Inventor: David F. Woodward, El Toro, Calif.

[73] Assignee: Allergan Sales, Inc., Irvine, Calif.

[21] Appl. No.: 07/975,194

[22] Filed: Nov. 12, 1992

[51] Int. Cl.[7] .......................... A61K 31/215; A61K 31/19
[52] U.S. Cl. ........................ 514/530; 514/573; 514/913
[58] Field of Search ..................................... 514/530, 573, 514/913

[56] References Cited

U.S. PATENT DOCUMENTS

| 4,599,353 | 7/1986 | Bito . |
| 4,994,274 | 2/1991 | Chan . |
| 5,139,491 | 8/1992 | Chan . |

FOREIGN PATENT DOCUMENTS

| 89/03384 | 5/1989 | WIPO . |
| 9119490 | 12/1991 | WIPO . |
| 9208465 | 5/1992 | WIPO . |
| 9210193 | 6/1992 | WIPO . |

OTHER PUBLICATIONS

AM. J. Physiol.,263(3,PT.2), H660–H663 1992 Banerjee, Mukul et al 'Effects of a novel prostaglandin, 8–epi–PGF2. alpha., in rabbit lung in situ'.

Prostaglandins, 44(2), 155–63 1992 Morrow, J.D. et al 'The F2–isoprostane, 8–epi–prostaglandin F2. alpha., a potent agonist of the vascular thromboxane/endoperoxide receptor, is a platelet thromboxane/endoperoxide receptor antagonist'.

Bito, L.Z., Prostaglandins and Related Compounds as Potential Ocular Therapeutic Agents; . Biological Protection with Prostaglandins, Cohen, M.M.; ed.; Boca Ratan, Fla, CRC Press, Inc., 1985, pp. 231–252.

Bito, L.Z., "Prostaglandins, Other Eicosanoids, and Their Derivatives as Potential Antiglaucoma Agents;"Applied Pharmacology in the Medical Treatment of Glaucomas, Drace, S.M. & Neufeld, A.H.eds., New York, Grune & Stratton, 1984, pp. 477–505.

Nilsson, et. al., "Increases Uveoscleral Outflow," Invest. Opthalmol. Vis.Sci, 28 (suppl), 284, 1987.

Bito, L.Z., "Prostaglandins, Old concepts and New Perspectives," Arch. Ophthalmol 105, 1036, 1987.

Siebold, et.al., "Esterified prostaglandin shows 'potent' promise," Prodrug, May 3, 1989.

*Primary Examiner*—Marianne Cintins
*Attorney, Agent, or Firm*—Robert J. Baran; Martin A. Voet; Carlos A. Fisher

[57] ABSTRACT

The present invention provides a method of treating ocular hypertension which comprises applying to the eye an amount sufficient to treat ocular hypertension of a compound of formula (I)

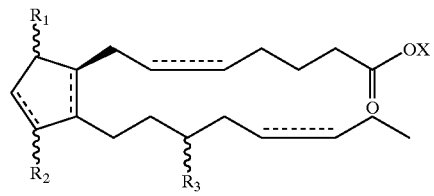

wherein the wavy line attachments indicate either alpha ($\alpha$) or beta ($\beta$) configuration; hatched lines indicate $\alpha$ configuration, solid triangles are used to indicate $\beta$ configuration; the dashed bonds represent a single bond or a double bond which can be in the cis or trans configuration; X is selected from the group consisting of H, R or a pharmaceutically-acceptable cation, and R is an aliphatic hydrocarbon group of about 1 to about 6 carbon atoms; one of $R_1$ and $R_2$ is =O, —OH or an —O(CO)$R_4$ group, and the other one is —OH or an —O(CO)$R_4$ group or $R_1$ is =O and $R_2$ is H; $R_3$ is —OH or —O(CO)$R_4$, wherein $R_4$ is a saturated or unsaturated acyclic hydrocarbon group having from 1 to about 20 carbon atoms, or —(CH$_2$)$_n$R$_5$ wherein n is 0–10, and $R_5$ is an aliphatic ring from about 3 to about 7 carbon atoms, or an aromatic or heteroaromatic ring; or a pharmaceutically acceptable salt thereof.

17 Claims, No Drawings

METHOD OF TREATING OCULAR HYPERTENSION WITH 8-EPI PROSTAGLANDINS

FIELD OF THE INVENTION

The present invention relates to 8-epi prostaglandins. More particularly, the present invention concerns 8-epi prostaglandins and C-1 ester derivatives thereof. Such compounds are potent ocular hypotensives, and are particularly suitable for the management of glaucoma.

BACKGROUND OF THE INVENTION

Ocular hypotensive agents are useful in the treatment of a number of ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Prostaglandins were earlier regarded as potent ocular hypertensives however evidence accumulated in the last decade shows that some prostaglandins are highly effective ocular hypotensive agents, and are ideally suited for the long-term medical management of glaucoma (see, for example, Bito, L. Z. *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins and their derivatives, in particular $PGE_2$ and $PGF_{2\alpha}$ and the $C_1$ to $C_5$ alkyl esters of the latter compound, were reported to possess ocular hypotensive activity and were recommended for use in glaucoma management. It was suggested that the $C_1$ to $C_5$ alkyl esters of $PGF_{2\alpha}$, such as its methyl and isopropyl esters, would be particularly advantageous due to their lipid-solubility which would permit more ready penetration through the cornea and would lower the effective amounts of these compounds.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported"[see, for example, Bito, L. Z., *Arch. Ophthalmol.* 105, 1036 (1987), and Siebold et al., *Prodrug* 5, 3 (1989)]. However, the use of $PGF_{2\alpha}$ 1-isopropyl ester or other C-1 alkyl esters in the clinical practice, is considerably limited by formulation difficulties due to their hydrophobic nature. Their ophthalmic formulations can only be made with oily carriers, such as sterile anhydrous peanut oil.

Also, whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed May 25, 1989). Similarly, 11,15- 9,15- and 9,11-diesters of prostaglandins, for example 11,15-dipivaloyl $PGF_{2\alpha}$ are known to have ocular hypotensive activity. See the co-pending patent applications U.S. Ser. Nos. 385,645, 386,312 and 386,834 (all filed Jul. 27, 1989). PGF 1-alcohols and their use as ocular hypotensives are disclosed in co-pending patent application U.S. Ser. No. 07/538,204 (filed Jun. 14, 1990). Other prostaglandin derivatives for ocular use are, for example, disclosed in U.S. Ser. No. 07/611,029 (filed Nov. 9, 1990), U.S. Ser. No. 07/624,659 (filed Dec. 10, 1990) and U.S. Ser. No. 07/623,234 (filed Dec. 6, 1990). The disclosures of these patent applications are hereby expressly incorporated by reference.

SUMMARY OF THE INVENTION

It has been surprisingly found that 8-epi prostaglandins and salts or C-1 esters thereof (i.e., prostaglandins wherein the carboxylic side chain is in the β configuration) exhibit essentially the same ocular hypotensive activity as the same compound wherein the carboxylic chain is in the α configuration, and cause significantly lower ocular surface hyperemia.

In one aspect, the present invention relates to a method of treating ocular hypertension which comprises applying to the eye an amount sufficient to treat ocular hypertension of a compound of formula (I)

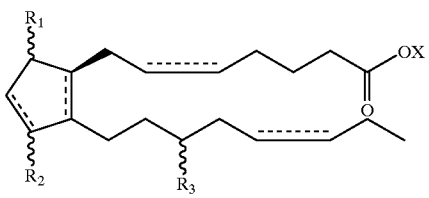

wherein the wavy line attachments indicate either alpha (α) or beta (β) configuration; hatched lines indicate α configuration, solid triangles are used to indicate β configuration; the dashed bonds represent a single bond or a double bond which can be in the cis or trans configuration; X is selected from the group consisting of H, R or a pharmaceutically-acceptable cation, and R is an aliphatic hydrocarbon group of about 1 to about 6 carbon atoms; one of $R_1$ and $R_2$ is =O, —OH or an —O(CO)$R_4$ group, and the other one is —OH or an —O(CO)$R_4$ group or $R_1$ is =O and $R_2$ is H; $R_3$ is —OH or —O(CO)$R_4$, wherein $R_4$ is a saturated or unsaturated acyclic hydrocarbon group having from 1 to about 20 carbon atoms, or —(CH$_2$)$_n$R$_5$ wherein n is 0–10, and $R_5$ is an aliphatic ring from about 3 to about 7 carbon atoms, or an aromatic or heteroaromatic ring; or a pharmaceutically acceptable salt thereof.

In a further aspect, the present invention relates to a pharmaceutical composition comprising an effective amount of a compound of formula (I) as hereinabove defined, or a pharmaceutically acceptable salt thereof.

In a preferred embodiment, such pharmaceutical compositions are in the form of ophthalmic solutions for the treatment of ocular hypertension, comprising an amount sufficient to treat ocular hypertension of a compound of formula (I) as hereinabove defined, or a pharmaceutically acceptable salt thereof.

The present invention further relates to pharmaceutical products comprising such ophthalmic solutions in a container adapted to dispense its contents in metered form.

DETAILED DESCRIPTION OF THE INVENTION

The present invention relates to 8-epi prostaglandins and esters and salts of said 8-epi prostaglandins.

Prostaglandins can be described as derivatives of prostanoic acid which has the following structural formula:

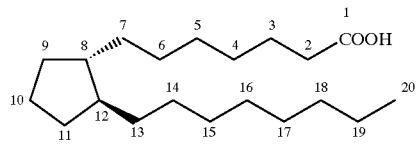

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ (PGE$_1$), prostaglandin $E_2$ (PGE$_2$)], and on the configuration of the substituents on the alicyclic ring indicated by α or β [e.g. prostaglandin $F_{2\alpha}$ (PGF$_{2\alpha}$)].

The prostaglandin derivatives according to the present invention are encompassed by the formula (I)

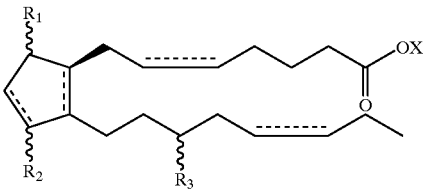

wherein the wavy line attachments indicate either alpha (α) or beta (β) configuration; hatched lines indicate α configuration, solid triangles are used to indicate β configuration; the dashed bonds represent a single bond or a double bond which can be in the cis or trans configuration; X is selected from the group consisting of H, R or a pharmaceutically-acceptable cation, and R is an aliphatic hydrocarbon group of about 1 to about 6 carbon atoms; Y is a polar functional group; one of $R_1$ and $R_2$ is =O, —OH or an —O(CO)$R_4$ group, and the other one is —OH or an —O(CO)$R_4$ group or $R_1$ is =O and $R_2$ is H; $R_3$ is —OH or —O(CO)$R_4$, wherein $R_4$ is a saturated or unsaturated acyclic hydrocarbon group having from 1 to about 20 carbon atoms, or —(CH$_2$)$_n$R$_5$ wherein n is 0–10, and $R_5$ is an aliphatic ring from about 3 to about 7 carbon atoms, or an aromatic or heteroaromatic ring; or a pharmaceutically acceptable salt thereof.

The above formula includes 8-epi prostaglandins of the F, D, E, A, B and J series. A preferred group of the compounds of the present invention is encompassed by the following formula (II)

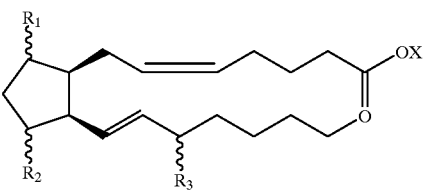

wherein $R_1$/$R_2$ is —OH/—OH, =O/—OH, —OH/=O (the —OH groups may be esterified) and the other symbols and substituents are as defined hereinabove. This definition includes PGF, PGE, and PGD derivatives.

Particularly preferred are the PGF$_{2\alpha}$ derivatives of the formula (III)

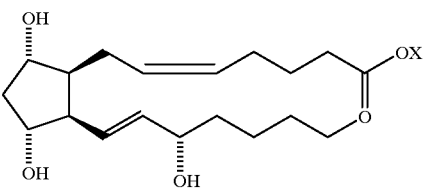

and their 9- and/or 11- and/or 15-esters.

In all of the above formulae, as well as in those provided hereinafter, the dotted lines on bonds between carbons 5 and 6 (C-5), between carbons 13 and 14 (C-13), between carbons 8 and 12 (C-8), between carbons 10 and 11 (C-10) and between carbons 17 and 18 (C-17) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

The naturally occurring stereochemistry of $PGF_{2\alpha}$ includes the C-9, C-11, and C-15 hydroxyl groups in the α configuration. In the compounds used in accordance with the present invention, however, prostaglandins having the C-9 or C-11 or C-15 substituents in β configuration are also contemplated. As hereinabove mentioned, in all formulas provided herein broken line attachments to the cyclopentane ring indicate substituents in the α configuration. Thickened solid line attachments to the cyclopentane ring indicate substituents in the β configuration. For instance, 9β-PGF compounds have the same structure as $PGF_\alpha$ compounds, except that the hydroxyl at the C-9 position is in the β configuration. Also, the broken line attachment of the hydroxyl group or other substituent to the C-11 and C-15 carbon atoms signifies the α configuration; therefore, compounds with the epi configuration for the hydroxyl group at C-15 are designated by using 15β and if there is no indication of the β configuration, the configuration is assumed α.

X is preferably H or a lower alkyl group, e.g., a $C_1$ to $C_3$ alkyl, i.e., methyl, ethyl, n-propyl or isopropyl.

In the substituent definitions, the "aliphatic hydrocarbon groups" have from 1 to about 6, most preferably 1 to about 4 carbon atoms. The aliphatic hydrocarbon groups may be straight or branched chained, saturated or unsaturated, such as straight or branched chained alkyl, alkenyl, alkynyl groups. Typical representatives of the alkyl groups include, for example, methyl, ethyl, n- and isopropyl, n-, sec-, iso- and tert-butyl, n- and isopentyl, n- and neohexyl, etc. groups. Typical alkenyl and alkynyl groups are vinyl, allyl, propenyl, ethynyl and propargyl.

The definition of $R_4$ may include a cyclic component, $-(CH_2)_nR_5$, wherein n is 0–10, $R_5$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, $R_5$ preferably is phenyl, and the heteroaromatic rings have oxygen, nitrogen or sulfur as a heteroatom. Preferably n is 0–4.

The most preferred compounds are those $PGF_{2\alpha}$ derivatives in which X is hydrogen or methyl.

The term "lower alkyl" alone or in combination with other moieties refers to alkyl groups having from one to about 6 carbon atoms. Preferred are the alkyl groups containing 1 to about 4, more preferably, 1 or 2 carbon atoms.

Particularly preferred are the following compounds:
8-epi $PGF_{2\alpha}$ and
8-epi $PGF_{2\alpha}$ 1-methyl ester The compounds of the present invention can be prepared by methods known in the art. In the case of 8-epi $PGF_{2\alpha}$, this was purchased from Cayman Chemical (Kalamazoo, Mich.).

A pharmaceutically acceptable salt is any salt which retains the activity of the parent compound and does not impart any deleterious or undesirable effect on the subject to whom it is administered and in the context in which it is administered. Of particular interest are the acid addition salts of the amine compounds of the present invention. Within this group, ophthalmically acceptable salts are those which do not impart any deleterious or undesirable effect when applied to the eye.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.8 with an appropriate buffer system, a substantially neutral pH being preferred. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–25 µl.

The invention is further illustrated by the following non-limiting Examples.

EXAMPLE 1

Intraocular Pressure-Reducing Activity

Experimental quantities of the test compounds were prepared in an ophthalmic formulation containing 0.1% polysorbate (Tween 80)–10 mM TRIS. One eye of each experimental animal was treated by applying one 25 µl drop of the drug formulation to the ocular surface, the contralateral eye received 25 µl of vehicle as a control. Intraocular pressure was measured by applanation pneumatonometry immediately before drug administration and at subsequent, predetermined times thereafter. New Zealand albino/dutch belted cross rabbits were employed as experimental animals.

The results are shown in Table 1 where the ocular hypotensive effects of 8-epi $PGF_{2\alpha}$ is compared to the naturally-occurring $PGF_2\alpha$. At a 0.1% concentration, the ocular hypotensive activity is essentially equivalent. However, the surface hyperemia of the 8-epi compound is much decreased.

TABLE 1

The effects of 8-epi $PGF_{2\alpha}$ and $PGF_{2\alpha}$ on rabbit intraocular pressure and ocular surface hyperemia
INTRAOCULAR PRESSURE
INTRAOCULAR PRESSURE (mmHg) CHANGES AT PREDETERMINED TIMES (HR) AFTER PROSTAGLANDIN ADMINISTRATION

| PROSTA-GLANDIN | Dose (%) | 1 HR | 2 HR | 3 HR | 4 HR | 6 HR |
|---|---|---|---|---|---|---|
| $PGF_{2\alpha}$ | 0.1% | +2.68* | −4.31* | −2.94* | −3.94** | −1.56 |
| 8-epi $PGF_{2\alpha}$ | 0.1% | −3.25** | −3.50* | −2.00 | −1.5 | −0.55 |

*p < 0.05
**p < 0.01
n = 4–6

OCULAR SURFACE HYPEREMIA
PERCENT ANIMALS EXHIBITING OCULAR SURFACE HYPEREMIA % HYPEREMIA AT PREDETERMINED TIMES (HR)

| PROSTA-GLANDIN | Dose (%) | 1 HR | 2 HR | 3 HR | 4 HR | 6 HR |
|---|---|---|---|---|---|---|
| $PGF_{2\alpha}$ | 0.1% | 100 | 100 | 87.5 | 100 | 75 |
| 8-epi $PGF_{2\alpha}$ | 0.1% | 83.3 | 50 | 66.6 | 17.7 | 0 |

It can be seen that although $PGF_{2\alpha}$ effectively lowered intraocular pressure, it caused persistent ocular surface hyperemia, whereas 8-epi $PGF_{2\alpha}$ was almost entirely devoid of this side effect. Thus, the favorable separation between ocular hypotension and ocular surface hyperemia is apparent.

EXAMPLE 2

The experiment was repeated with monkeys as experimental animals. These results which show that the 8-epi $PGF_{2\alpha}$ is effective in lowering IOP are reported in Table 2.

TABLE 2

The effects of 8-epi $PGF_{2\alpha}$ (0.1%) on monkey intraocular pressure

| | TIME (HR) | | | |
|---|---|---|---|---|
| | 2 HR | 3 HR | 4 HR | 6 HR |
| IOP (mmHg) | +1.17 | − | −1.00** | −1.83** |

**p < 0.01

EXAMPLE 3

Intraocular Pressure-Reducing Activity

The effects of the methyl ester of the 8-epi $PGF_{2\alpha}$ on monkey intraocular pressure are shown in Table 3. The results show that this compound is effective in lowering IOP.

TABLE 3

Effect of 8-epi $PGF_{2\alpha}$-1-methyl ester, given topically twice a day to monkey eyes, on intraocular pressure

| TIME (HRS AFTER TOPICAL ADMINISTRATION) | NET DECREASE IN INTRAOCULAR PRESSURE (mmHg) |
|---|---|
| 2 | −0.83 |
| 4 | −1.00 |
| 24 | −0.83 |
| 26 | −0.5 |
| 28 | −0.83 |
| 30 | −0.67 |
| 48 | −1.0 |
| 50 | −1.5 |
| 52 | −2.17* |
| 54 | −1.33 |
| 72 | −1.50* |
| 74 | −2.00** |
| 76 | −2.50** |
| 78 | −2.50** |
| 96 | −2.00* |
| 98 | −1.17** |
| 100 | −2.17* |
| 102 | −2.50** |

*p < 0.05
**p < 0.01
n = 6

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension which comprises applying to the eye an amount sufficient to treat ocular hypertension of a compound of formula (I) while lowering hyperemia as compared to the corresponding iso form of the compound

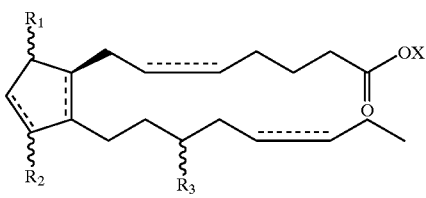

wherein the wavy line attachments indicate either alpha (α) or beta (β) configuration; hatched lines indicate α configuration, solid triangles are used to indicate β configuration; the dashed bonds represent a single bond or a double bond which can be in the cis or trans configuration; X is selected from the group consisting of H, R or a pharmaceutically-acceptable cation, and R is an aliphatic hydrocarbon group of about 1 to about 6 carbon atoms; one of $R_1$ and $R_2$ is =O, —OH or an —O(CO)$R_4$ group, and the other one is —OH or an —O(CO)$R_4$ group or $R_1$ is =O and $R_2$ is H; $R_3$ is —OH or —O(CO)$R_4$, wherein $R_4$ is a saturated or unsaturated acyclic hydrocarbon group having from 1 to about 20 carbon atoms, or —(CH$_2$)$_n$R$_5$ wherein n is 0–10, and $R_5$ is an aliphatic ring from about 3 to about 7 carbon atoms, or an aromatic ring; or a pharmaceutically acceptable salt thereof.

2. The method of claim 1 wherein said compound is applied to the eye as an aqueous ophthalmic solution comprising said compound in a concentration of about 0.0001 to about 5% (w/v).

3. The method of claim 2 wherein said concentration is about 0.001 to about 1.0% (w/v).

4. The method of claim 3 wherein the pH of said ophthalmic solution is maintained between about 6.5 and about 7.8.

5. The method of claim 1 wherein said compound of formula (I) is selected from the group consisting of naturally occurring prostaglandins of the D, E and F series.

6. The method of claim 1 wherein said compound is a PG derivative of the formula (II)

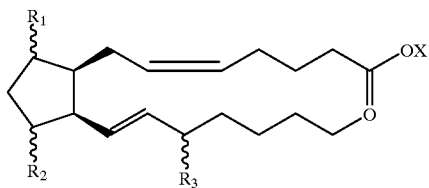

wherein X and $R_3$ are as defined in claim 1 and $R_1/R_2$ is —OH/—OH, =O/—OH, —OH/=O, or a —O(CO)$R_4$ ester thereof.

7. The method of claim 1 wherein said compound is a PGF$_{2\alpha}$ derivative of the formula (III)

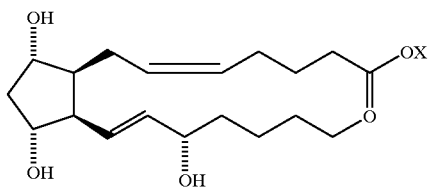

wherein X and the other symbols are as defined in claim 1.

8. The method of claim 7 wherein said compound of formula (I) is selected from the group consisting of 8-epi-PGF$_{2\alpha}$ and
PGF$_{2\alpha}$ 1-methyl ester,
and a pharmaceutically acceptable salt thereof.

9. A pharmaceutical composition comprising an effective amount of a compound of formula (I) while lowering hyperemia as compared to the corresponding iso form of the compound

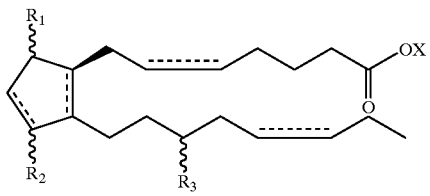

wherein the wavy line attachments indicate either alpha (α) or beta (β) configuration; hatched lines indicate α configuration, solid triangles are used to indicate β configuration; the dashed bonds represent a single bond or a double bond which can be in the cis or trans configuration; X is selected from the group consisting of H, R and pharmaceutically-acceptable cations and R is an aliphatic hydrocarbon group of about 1 to about 6 carbon atoms; one of $R_1$ and $R_2$ is =O, —OH or an —O(CO)$R_4$ group, and the other one is —OH or an —O(CO)$R_4$ group or $R_1$ is =O and $R_2$ is H; $R_3$ is —OH or —O(CO)$R_4$, wherein $R_4$ is a saturated or unsaturated acyclic hydrocarbon group having from 1 to about 20 carbon atoms, or —(CH$_2$)$_n$R$_5$ wherein n is 0–10, and $R_5$ is an aliphatic ring from about 3 to about 7 carbon atoms, or an aromatic ring; or a pharmaceutically acceptable salt thereof, in admixture with a non-toxic pharmaceutical carrier.

10. The pharmaceutical composition of claim 9 in the form of an aqueous solution.

11. The pharmaceutical composition of claim 10 wherein said aqueous solution is an ophthalmic solution for the treatment of ocular hypertension comprising an amount sufficient to treat ocular hypertension of said compound of formula (I) or an ophthalmically acceptable salt thereof.

12. The pharmaceutical composition of claim 11 wherein said ophthalmic solution comprises about 0.001 to about 1.0% (w/v) of said compound of formula (I) of an ophthalmically acceptable salt thereof.

13. The pharmaceutical composition of claim 12 wherein the pH of said ophthalmic solution is maintained between about 6.5 and about 7.8.

14. The pharmaceutical composition of claim 13 wherein said compound is a PGF$_{2\alpha}$ derivative of the formula (m)

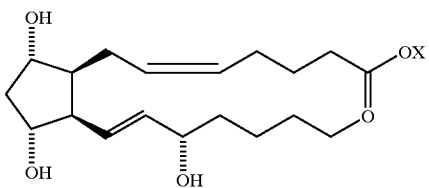

wherein X and the other symbols are as defined in claim 9.

15. The pharmaceutical composition of claim 14 wherein said compound of formula (I) is selected from the group consisting of 8-epi PGF$_{2\alpha}$ and
8-epi PGF$_{2\alpha}$ 1-methyl ester and
an ophthalmically acceptable salt thereof.

16. An ophthalmic solution comprising a therapeutically effective amount of a compound of formula (I) while lowering hyperemia as compared to the corresponding iso form of the compound

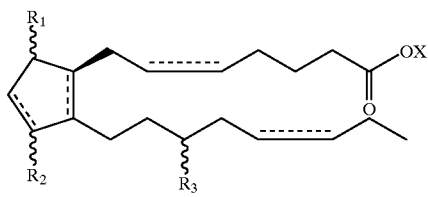

wherein the wavy line attachments indicate either alpha (α) or beta (β) configuration; hatched lines indicate α configuration, solid triangles are used to indicate β configuration; the dashed bonds represent a single bond or a double bond which can be in the cis or trans configuration; X is selected from the group consisting of H, R and pharmaceutically-acceptable cations and R is an aliphatic hydrocarbon group of about 1 to about 6 carbon atoms; one of $R_1$ and $R_2$ is =O, —OH or an —O(CO)$R_4$ group, and the other one is —OH or an —O(CO)$R_4$ group or $R_1$ is =O and $R_2$ is H; $R_3$ is —OH or —O(CO)$R_4$, wherein $R_4$ is a saturated or unsaturated acyclic hydrocarbon group having from 1 to about 20 carbon atoms, or —(CH$_2$)$_n$R$_5$ wherein n is 0–10, and $R_5$ is an aliphatic ring from about 3 to about 7 carbon atoms, or an aromatic ring; or a pharmaceutically acceptable salt thereof as defined in claim 1, or an ophthalmically acceptable salt thereof, in admixture with a non-toxic, ophthalmically acceptable liquid vehicle, packaged in a container suitable for metered application.

17. A pharmaceutical product, comprising a container adapted to dispense the contents of said container in metered form; and an ophthalmic solution in said container as defined in claim 16.

* * * * *

UNITED STATES PATENT AND TRADEMARK OFFICE
CERTIFICATE OF CORRECTION

PATENT NO. : 6,124,353
DATED : September 26, 2000
INVENTOR(S) : Woodward

It is certified that error appears in the above-indentified patent and that said Letters Patent is hereby corrected as shown below:

Column 5, line 5; delete "a" and insert in place thereof -- --

Column 10, line 50; delete "(m)" and insert in place thereof --(III)--

Signed and Sealed this

Fifteenth Day of May, 2001

Attest:

NICHOLAS P. GODICI

*Attesting Officer*     *Acting Director of the United States Patent and Trademark Office*